United States Patent [19]

Manicom

[11] Patent Number: 5,755,692
[45] Date of Patent: May 26, 1998

[54] METHOD AND APPARATUS FOR ADMINISTERING A DRUG TO A PATIENT

[76] Inventor: Anthony William Manicom, 173 Blandford Road, North Riding, Randburg, South Africa

[21] Appl. No.: 647,942

[22] PCT Filed: Sep. 27, 1995

[86] PCT No.: PCT/GB95/02296

§ 371 Date: May 28, 1996

§ 102(e) Date: May 28, 1996

[87] PCT Pub. No.: WO96/09844

PCT Pub. Date: Apr. 4, 1996

[30] Foreign Application Priority Data

Sep. 28, 1994 [ZA] South Africa ............... 94/7542

[51] Int. Cl.$^6$ ............... A61M 1/00; A61M 37/00
[52] U.S. Cl. ............... 604/152; 604/82; 604/83; 604/131; 604/151; 604/208; 604/246
[58] Field of Search ............... 604/83–89, 31, 604/65, 67, 71, 118, 120, 121, 131, 151, 152, 154, 155, 207, 208, 214, 218, 232, 235, 246

[56] References Cited

U.S. PATENT DOCUMENTS

| | | | |
|---|---|---|---|
| 3,515,127 | 6/1970 | Reymond | 604/152 X |
| 4,065,230 | 12/1977 | Gezari | 604/152 X |
| 4,196,730 | 4/1980 | Wilson | 128/214 |
| 4,345,595 | 8/1982 | Whitney et al. | 604/152 |
| 4,475,666 | 10/1984 | Bilbrey et al. | 604/152 X |
| 5,069,668 | 12/1991 | Boydman | 604/121 |
| 5,188,604 | 2/1993 | Orth | 604/153 |

FOREIGN PATENT DOCUMENTS

| | | |
|---|---|---|
| 556878 | 8/1993 | European Pat. Off. |
| 619122 | 10/1994 | European Pat. Off. |
| 2066669 | 7/1981 | United Kingdom. |

OTHER PUBLICATIONS

Cook and Whitman, "Patient Controlled Sedation" pp. 275–288.
Cook and Whitman, "New Procedures—New Sedation Techniques" Minimally Invasive Therapy 1994:3 (Suppl. 2): 39–42.

*Primary Examiner*—Sam Rimell
*Assistant Examiner*—Robert V. Racunas
*Attorney, Agent, or Firm*—Felfe & Lynch

[57] ABSTRACT

A method of administering a drug to a patient comprises the steps of filling a dispenser (20) with a predetermined total volume of a liquid containing the drug and administering a predetermined volume of the liquid in the dispenser to the patient (10) The liquid in the dispenser is then replaced with a diluent (22). The administration of liquid and replacement with diluent (22) are then repeated from time to time so that diminishing doses of the drug are administered to the patient (10). Preferably the diluent (22) is drawn into the dispenser (20) prior to the drug containing liquid being administered. The method is preferably- patient (10) controlled via control push button (48). The invention extends to apparatus which is used to carry out the method.

7 Claims, 4 Drawing Sheets

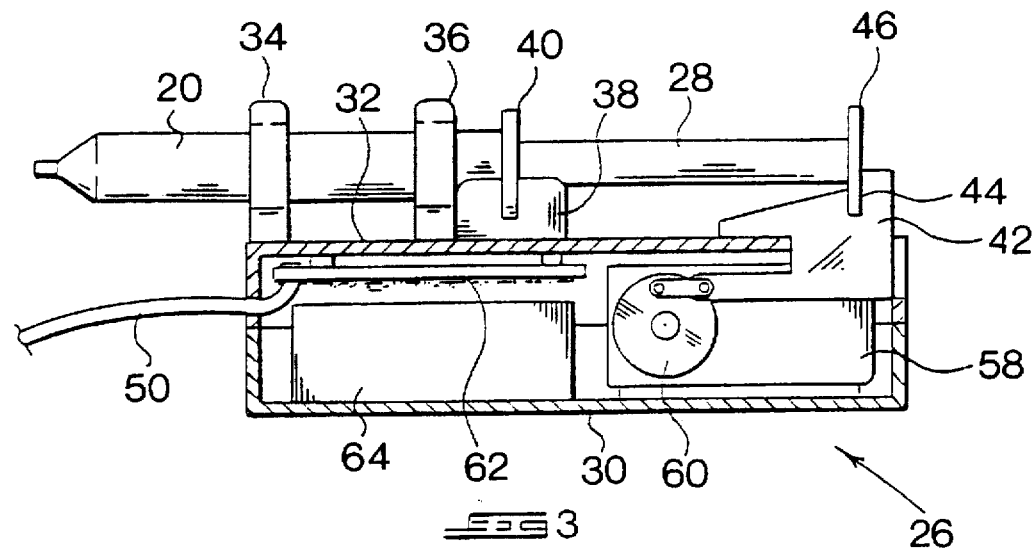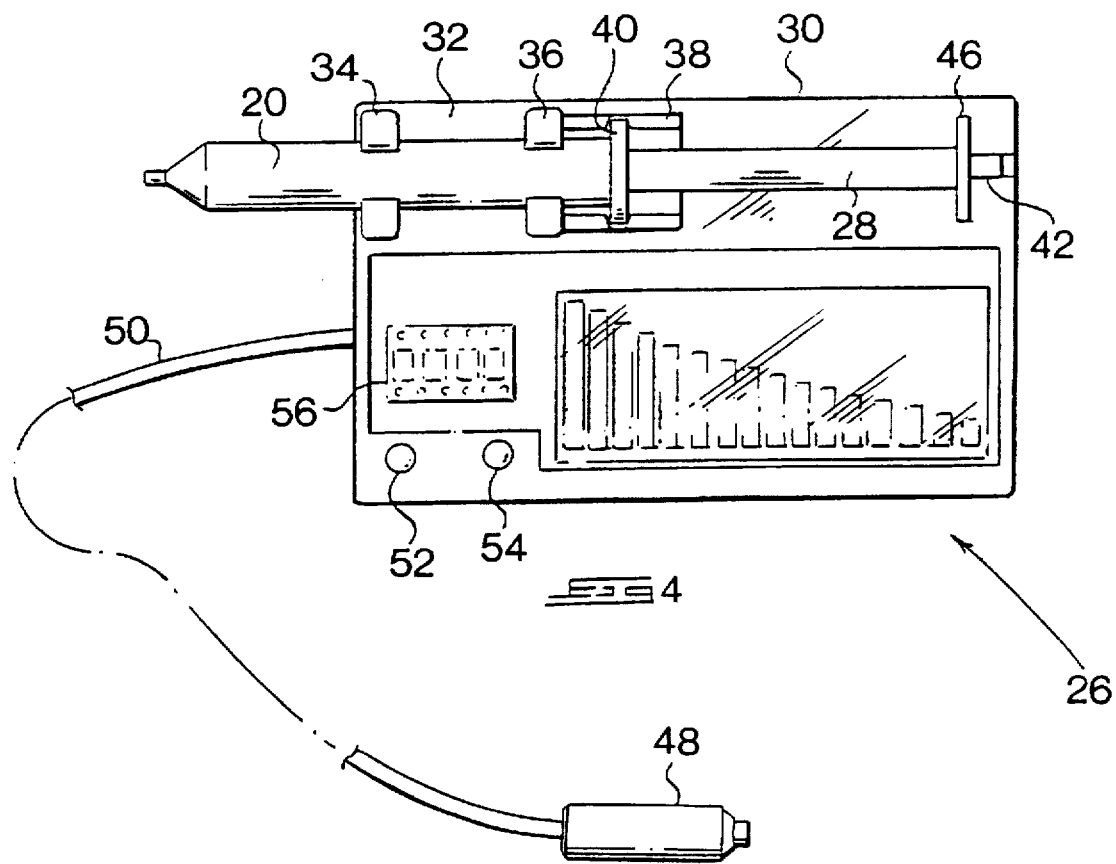

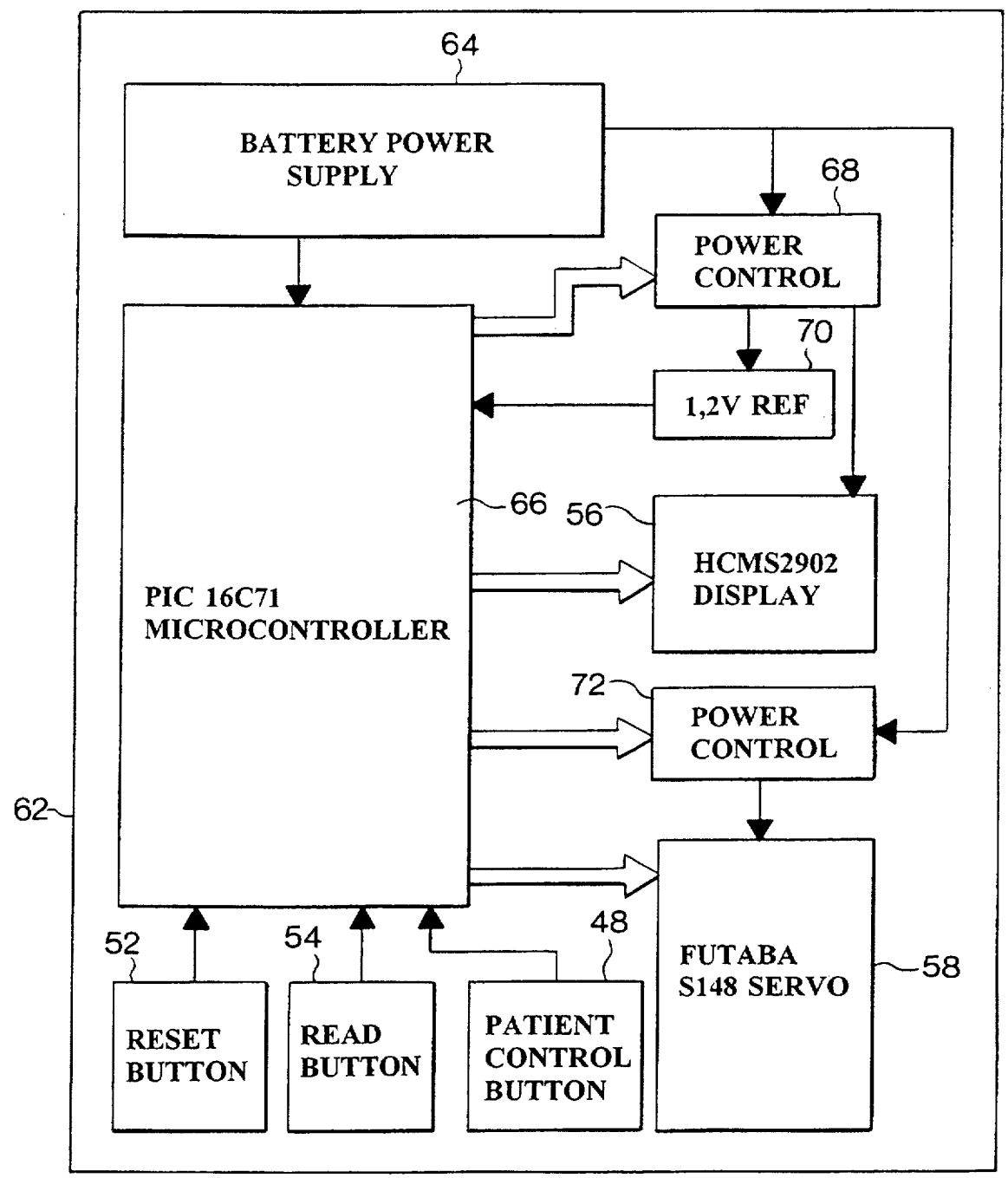

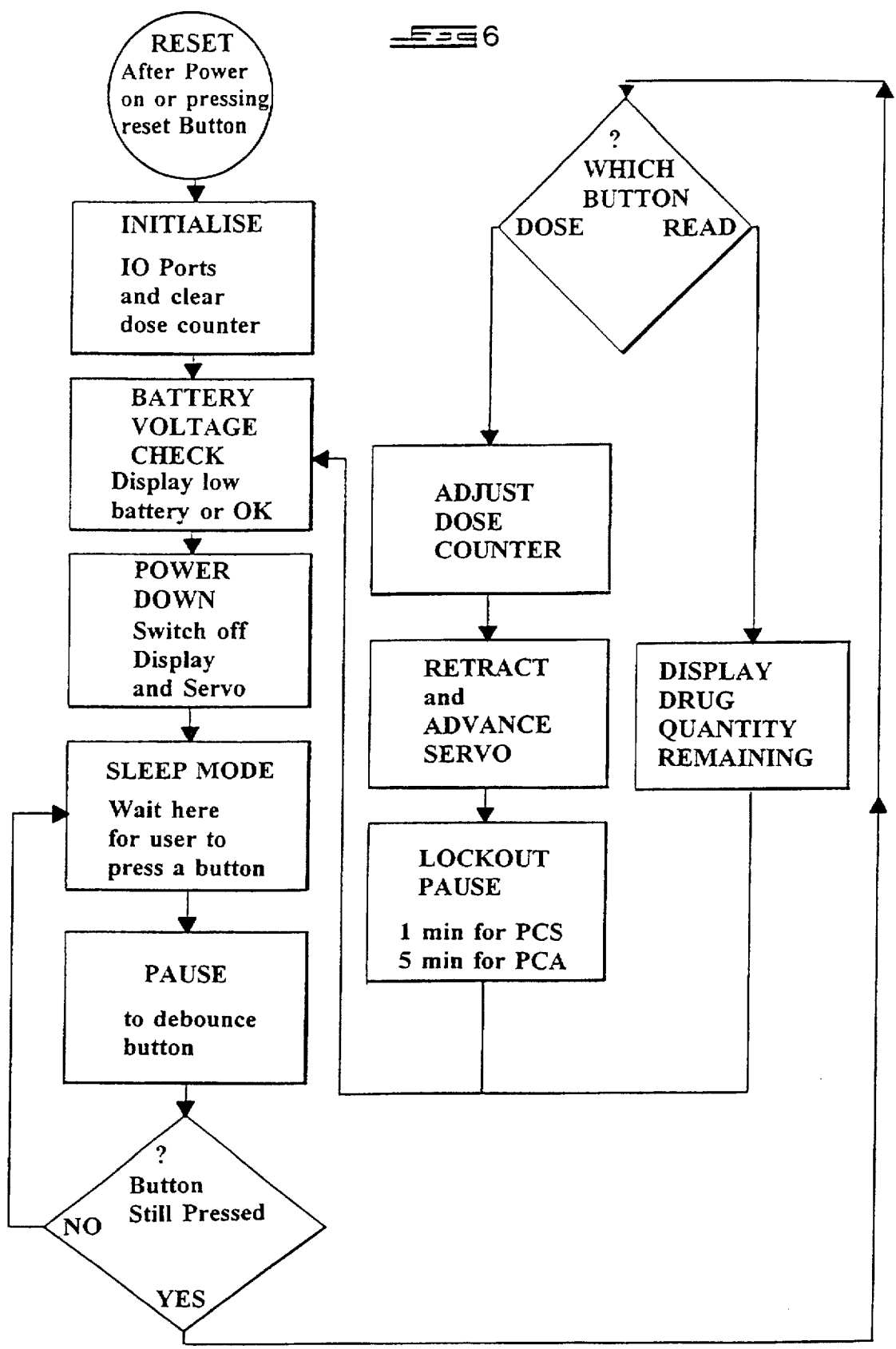

METHOD AND APPARATUS FOR ADMINISTERING A DRUG TO A PATIENT

BACKGROUND OF THE INVENTION

This invention relates to a method of and apparatus for administering a drug to a patient.

The use of patient controlled analgesia and sedation (PCA and PCS) has gained acceptance in the medical field, but PCA and PCS systems must be carefully designed to avoid the possibility of accidents or deliberate overdoses. Such equipment should also be simple to use. The advantages of patient responsive liquid medium delivery systems and the background to the development of such a system are described in some detail in U.S. Pat. No. 5,064,668 which is incorporated herein by way of reference. However, prior art systems known to applicant tend to be costly and complex, which makes the use of such systems inappropriate for use in less affluent or sophisticated societies. Indeed, it would be desirable for the system to be widely available, possibly even on an out patient basis, but in that event the system would need to incorporate safety features which would protect the patient against overdose as a consequence of malfunction or misuse.

SUMMARY OF THE INVENTION

According to the invention a method of administering a drug to a patient comprises the steps of:

(a) filling a dispenser with a predetermined total volume of a liquid containing the drug;

(b) administering a predetermined volume of the liquid in the dispenser to the patient;

(c) replacing the volume of liquid administered to the patient with a diluent; and (d) repeating steps (b) and (c) from time to time so that a plurality of diminishing doses of the drug are administered to the patient Preferably, the dispenser is a syringe, the plunger of which is operated with a reciprocating movement from time to time to administer the predetermined volume of the liquid to the patient, and to draw an equal volume of the diluent into the syringe from a diluent reservoir. The preferred arrangement is for the diluent to be drawn into the dispenser prior to the administration of the liquid to the patient.

The travel of the plunger may be constant for each reciprocation thereof.

The plunger may be moved by an electromechanical actuator such as a servomotor or a solenoid in response to an electrical drive signal. Further according to the invention apparatus for administering a drug to a patient comprises:

support means for supporting a syringe, the syringe having a cylinder and a plunger movable in the cylinder, actuator means engagable with the plunger to move it into and out of the cylinder; and control means for generating drive signals at intervals to which the actuator means is responsive to cause a reciprocating movement of the plunger in the cylinder from time to time, thereby to cause the plunger to perform a delivery stroke during which a quantity of a liquid in the cylinder is expelled, and an intake stroke in which a quantity of a diluent liquid is drawn into the cylinder.

The actuator means may comprise a solenoid or servomotor arranged to move the plunger a predetermined distance into and out of the cylinder during each reciprocation thereof, so that an equal volume of liquid is expelled from and drawn into the cylinder during each reciprocation. The intake stroke may take place prior to the delivery stroke so that diluent liquid is drawn into the syringe prior to delivery. A time delay facility may be incorporated into the control means to provide for a time delay between the intake stroke and the delivery stroke to allow for mixing of drug and diluent prior to delivery.

The apparatus preferably includes operating means operable by a patient to generate a demand signal to which the control means is responsive to generate the drive signal The control means may include timing means for determining a minimum duration of the intervals between the generation of each drive signal. The apparatus may include display means for displaying data indicative of the amount of the origin liquid remaining in or dispensed from the syringe, corresponding to the overall dose of the drug in the liquid remaining or already dispensed from the syringe, or which indicates the number of operations of the actuator.

BRIEF DESCRIPTION OF THE DRAWINGS

The invention will now be described in more detail, by way of example only, with reference to the accompanying drawings in which:

FIG. 3 is a partial sectional side view of the apparatus of the invention;

FIG. 4 is a plan view of the apparatus of FIG. 3;

FIG. 5 is a simplified block schematic diagram of the electronic circuitry of the apparatus of FIGS. 3 and 4; and FIG. 6 is a simplified flow chart illustrating the operation of the apparatus in use.

DESCRIPTION OF THE EMBODIMENTS

Figure 1:
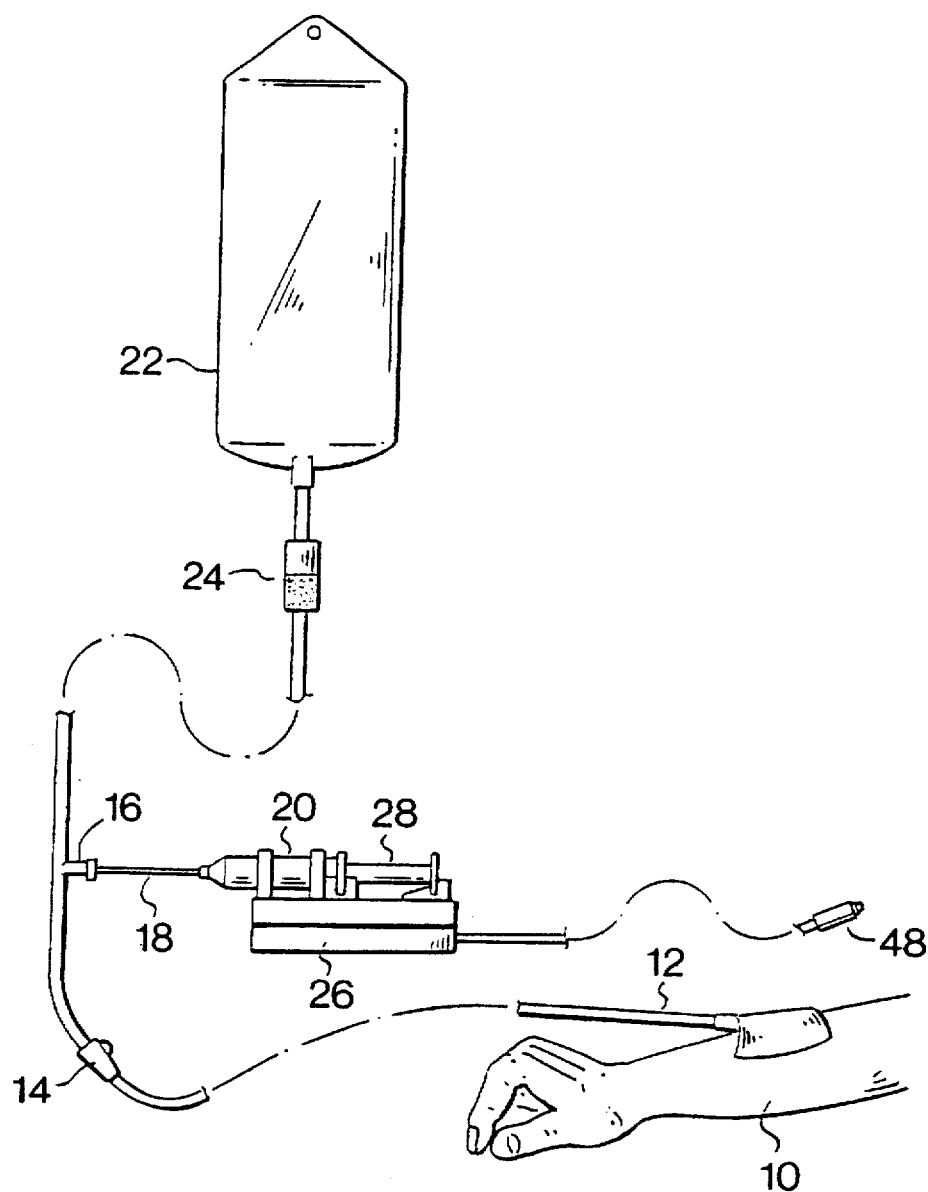
FIG. 1 is a schematic illustration of an arrangement for exercising the method of the invention, incorporating apparatus according to the invention.

Referring first to FIG. 1, a patient 10 is fitted with a catheter 12 which is connected via a flow control device 14 to a T-connector 16. An injection port at one branch of the T-connector receives the needle 18 of a syringe 20, while the other branch of the T is connected to a drip bag 22 of saline solution or another diluent via a flow control device 24.

The syringe 20 is mounted on apparatus according to the invention, illustrated schematically at 26, which is operated by the patient in a patient controlled analgesia (PCA) or patient controlled sedation (PCS) scheme to administer a drug to the patient.

The syringe 20 is primed with a predetermined volume of a drug in liquid form which is equal to, say, ten times the estimated first dose requirement. All air is expelled from the syringe, which is then coupled to the injection port of the T-piece 16 and then clamped or clipped to the apparatus 26. If necessary, the plunger 28 of the syringe is withdrawn, entraining infusion fluid. The flow control device 24 is adjusted to control the infusion flow rate to a rate sufficient to allow flushing of any drug released from the syringe to the patient The apparatus 26 is illustrated physically in FIGS. 3 and 4, while its electronic circuitry is illustrated in FIG. 5. The apparatus comprises a housing 30, typically a two-part plastics box. Fixed to the upper surface 32 of the box are a pair of spring clips 34 and 36, and a slotted retaining formation 38 which is shaped to receive the base flange 40 of the syringe cylinder, so that the syringe is positively located on the apparatus in use.

Towards one end of the housing is a drive element 42 in a form of a plastics plate, with a slot 44 in which the end flange 46 of the syringe plunger 28 is located. When the syringe is clamped to the apparatus, the volume of liquid in the syringe is approximately nine tenths of its nominal capacity.

The apparatus has three controls, being a push button or bell push 48 connected to the housing by a cable 50, operable by the patient to cause the apparatus to dispense a dose of the drug, a "reset" push button 52 and a "read" push button 54. The apparatus includes a display 56 which is typically a 4-character miniature alphanumeric display Within the housing is an electromechanical actuator, typically a servomotor 58, with a drive link 60 connected pivotally to the drive element 42 A servomotor is useful in that it can be adjusted to cause movement of the drive member 42 which is repeatable, but which can be varied by the control circuitry of the apparatus for different requirements Instead of a servomotor, a solenoid with a repeatable stroke could be used instead.

The operation of the servomotor 58 is controlled by an electronic circuit 62 which is powered by a battery 64.

The electronic circuitry is illustrated schematically in FIG. 5, and comprises a microcontroller 66, which in the prototype was a type PICl6C71 device. In addition to the components already described above, the electronic circuitry includes a first power control circuit 68 with a voltage reference circuit 70, which monitors the battery output voltage and compares it with a 1.2 volt reference voltage, to ensure that the supply voltage to the circuit is adequate. The circuit also includes a second power control or drive circuit 72 which in the prototype comprise power transistors which deliver current pulses to the servomotor 58 in response to control signals from the microcontroller 66.

The microcontroller 66 has an integral ROM and RAM memory, with a program to control the operation of the apparatus being stored in the ROM.

In operation, once the syringe has been fitted to the apparatus, the re-set button 52 is pressed, which resets the dose count displayed on the display 56 and enables the apparatus. Once the apparatus has been initialized, the display and other non-essential circuits are powered down, and the microcontroller enters a "sleep" state in which it waits for a demand signal from the push button 48.

When a demand signal is detected, the microcontroller outputs a pulse train with a first pulse width, causing the drive circuit 72 to operate the servomotor and thus to withdraw the drive element 42 a predetermined distance, causing an intake stroke of the plunger and drawing into the cylinder a predetermined volume of the diluent into the cylinder of the syringe. The microcontroller will then hold the plunger in this position for a period of approximately five seconds to allow mixing of drug and diluent within the cylinder of the syringe. After the intake stroke, the microcontroller outputs a pulse train with a second pulse width, causing the drive element 44 to reverse its movement and causing the plunger to perform a delivery stroke. The delivery stroke is of the same length as the intake stroke so that the volume of drug and diluent mix dispersed is the same as the volume of diluent drawn into the syringe. It is preferred that the intake stroke takes place before the delivery stroke so that during the "lock out" phase referred to below the drug has sufficient time to pass into the patient before the next intake stroke takes place. This prevents the drug being drawn back into the syringe from the catheter 12 during the intake stroke. It would, of course, be possible to reverse the order of the strokes by incorporating a oneway valve into the catheter 12 near to the syringe.

Once this intake delivery cycle has been completed, a "lock out" timer operates, disabling the apparatus for a predetermined period, typically 5 minutes in the case of PCA applications, or 1 minute in the case of PCS applications using short acting drugs, during which period the apparatus will not respond to further operation of the patient control button 48. This prevents a patient from deliberately or inadvertently administering an excessive dose of the drug. The lock Out period provides the time required for flushing the drug to the patient even with relatively slow flowing infusions.

Once the lock out time period has passed, the micro processor reverts to its "sleep" cycle, waiting for a further demand signal from the patient control push button 48.

Figure 2:
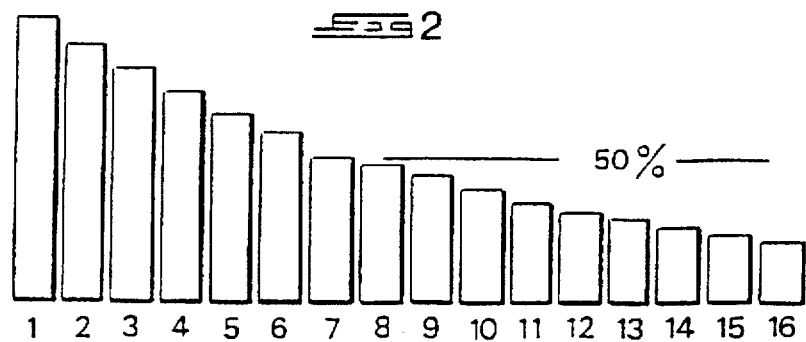
FIG. 2 is a graph illustrating schematically the relative magnitude of successive doses of a drug administered to a patient using the method of the invention.

Due to the fact that a volume of diluent is drawn into the syringe prior to each drug dose being administered, the concentration of the drug in the syringe gradually decreases, and each successive dose administered by the apparatus is slightly smaller, as indicated in FIG. 2. The strength of the drug dose delivered by the apparatus decreases exponentially, although the volume dispensed each time is constant. For example, if the syringe were to be primed with 15 mg of a sedative drug, and the delivery stroke discharged 10% of the total volume of the syringe, the first demand signal would result in delivery of 1.5 mg of the drug, the second demand would result in delivery of 1.35 mg, and successive doses would be 1.22 mg, 1.09 mg, 0.98 mg, 0.89 mg, and so on. It is known in the art that a diminishing concentration drug supply arrangement has a number of distinct advantages. See for example U.S. Pat. No. 4,623, 334. The present invention achieves a diminishing supply arrangement but on a patient controlled basis.

The microcontroller counts the number of operations of the servomotor, and can generate a display of the number of actuations of the device, or can calculate either the amount of the drug administered or remaining in the syringe.

The flow chart of FIG. 6 summarizes the operation of the apparatus graphically.

Because the described apparatus uses relatively small drug quantities, and has an inherent immunity to accidental siphonage, it is relatively safe compared with presently used large reservoir techniques, where serious overdosage is possible. The device does not require to be programmed, so that the likelihood of operator error by medical staff is also reduced. The device can be constructed so as to operate with standard sterile syringes so that no special container or sterilization apparatus is required. The simplicity of the drive system and control arrangement will be immediately apparent enabling the apparatus to be constructed inexpensively. The inherent safety of the system and its low cost makes the system attractive for use in many applications but particularly in less affluent communities where patient care cost is an important consideration when deciding what treatment a patient will be given.

I claim:

1. An apparatus for administering a drug to a patient comprising:

a reservoir of diluent liquid, support means supporting a syringe, the syringe having a cylinder and a plunger movable in the cylinder;

actuator means engagable with the plunger to move the plunger into and out of the cylinder; and control means for generating drive signals at intervals to which the actuator means is responsive to cause a reciprocating movement of the plunger in the cylinder, thereby causing the plunger to perform a delivery stroke during which a quantity of a drug in the cylinder is expelled, and an intake stroke in which a quantity of a diluent liquid is drawn into the cylinder.

2. The apparatus according to claim 1 wherein the actuator means comprises a solenoid or servomotor arranged to move the plunger a predetermined distance into and out the cylinder during each reciprocation thereof, so that an equal volume of liquid is expelled from and drawn into the cylinder during each reciprocation.

3. The apparatus according to claim 1 wherein the control means functions in a manner such that the intake stroke takes place prior to the delivery stroke for each reciprocation.

4. The apparatus according to claim 3 wherein the control means includes an automatic time delay facility for delaying the delivery stroke after the intake stroke has been completed.

5. The apparatus according to claim 1 including operating means operable by a patient to generate a demand signal to which the control means is responsive to generate the drive signal.

6. The apparatus according to claim 5 wherein the control means includes timing means for determining a minimum duration of the intervals between the generation of each drive signal.

7. The apparatus according to claim 1 including display means for displaying data indicative of the amount of the liquid remaining in or dispensed from the syringe, or the number of operations of the actuator.

* * * * *

UNITED STATES PATENT AND TRADEMARK OFFICE
CERTIFICATE OF CORRECTION

PATENT NO. : 5,755,692
DATED : May 26, 1998
INVENTOR(S) : Anthony W. MANICOM

It is certified that error appears in the above-identified patent and that said Letters Patent is hereby corrected as shown below:

In column 1, line 14, change "5,064,668" to -- 5,069,668 --.

In column 3, line 20, before "Instead" insert -- . --.

Signed and Sealed this

Thirteenth Day of June, 2000

Attest:

Q. TODD DICKINSON

Attesting Officer

Director of Patents and Trademarks